United States Patent
Kadziauskas et al.

(10) Patent No.: US 6,579,255 B2
(45) Date of Patent: Jun. 17, 2003

(54) PRESSURIZED FLOW OF FLUID INTO THE EYE USING PUMP AND PRESSURE MEASUREMENT SYSTEM

(75) Inventors: Kenneth E. Kadziauskas, Coto de Caza, CA (US); Mark S. Cole, Trabuco Canyon, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 09/918,749

(22) Filed: Jul. 31, 2001

(65) Prior Publication Data

US 2003/0028141 A1 Feb. 6, 2003

(51) Int. Cl.$^7$ .................................................. A61M 1/00
(52) U.S. Cl. ........................... 604/35; 604/67; 604/119; 606/107
(58) Field of Search ................................ 604/27, 28, 30, 604/31, 35, 43, 65–67, 93.01, 118, 119, 246, 247; 606/107

(56) References Cited

U.S. PATENT DOCUMENTS

| | | | | |
|---|---|---|---|---|
| 3,693,613 A | * | 9/1972 | Kelman | 606/169 |
| 3,812,855 A | * | 5/1974 | Banko | 604/31 |
| 4,052,987 A | * | 10/1977 | Wuchinich et al. | 604/65 |
| 4,156,187 A | * | 5/1979 | Murry et al. | 324/142 |
| 4,180,074 A | * | 12/1979 | Murry et al. | 604/31 |
| 4,841,984 A | * | 6/1989 | Armeniades et al. | 600/561 |
| 5,242,404 A | * | 9/1993 | Conley et al. | 604/119 |
| 5,429,601 A | * | 7/1995 | Conley et al. | 604/65 |
| 5,624,394 A | * | 4/1997 | Barnitz et al. | 604/67 |
| 5,649,905 A | * | 7/1997 | Zanger et al. | 604/34 |
| 5,676,650 A | * | 10/1997 | Grieshaber et al. | 604/28 |
| 5,700,240 A | * | 12/1997 | Barwick, Jr. et al. | 604/22 |
| 5,733,256 A | * | 3/1998 | Costin | 604/22 |
| 5,795,328 A | * | 8/1998 | Barnitz et al. | 604/67 |
| 5,810,765 A | * | 9/1998 | Oda | 604/31 |
| 5,830,176 A | * | 11/1998 | Mackool | 604/22 |
| 5,910,110 A | * | 6/1999 | Bastable | 600/398 |
| 6,083,193 A | * | 7/2000 | Kadziauskas et al. | 604/22 |
| 6,159,175 A | * | 12/2000 | Strukel et al. | 604/22 |
| 6,179,808 B1 | | 1/2001 | Baukhny et al. | 604/65 |
| 6,241,700 B1 | * | 6/2001 | Leukanech | 604/19 |
| 6,261,283 B1 | * | 7/2001 | Morgan et al. | 604/540 |
| 6,261,297 B1 | * | 7/2001 | Kadziauskas et al. | 606/107 |

* cited by examiner

Primary Examiner—Ira S. Lazarus
Assistant Examiner—Andrea M. Ragonese
(74) Attorney, Agent, or Firm—Walter A. Hackler; Peter Jon Gluck

(57) ABSTRACT

A method and apparatus provided for controlling fluid control to and from an eye or a phacoemulsification handpiece. The handpiece includes an ultrasonically driven, hollow, sleeved needle and the method includes inserting the needle and sleeve into an eye for phacoemulsification of eye tissue and introducing fluid into the eye through an annulus established between the sleeve and the needle. Aspiration of fragmented tissue and fluid from the eye is conducted through the hollow needle. An initial irrigation fluid pressure is determined and the irrigation fluid flow and aspiration fluid flow are adjusted based upon the initial determination. Thereafter continued determination of irrigation fluid pressure is utilized to continuously adjust irrigation fluid flow and/or aspiration fluid flow.

3 Claims, 2 Drawing Sheets

PRESSURIZED FLOW OF FLUID INTO THE EYE USING PUMP AND PRESSURE MEASUREMENT SYSTEM

The present invention generally relates to a method and apparatus for ophthalmic surgery. More specifically, the present invention is directed to a method and apparatus for controlling fluid flow to and from an eye during ophthalmic surgery.

In retinal and vitreous surgery, a separate needle is used to supply infusion, or irrigation, fluid or suction, for aspiration, respectively.

Phacoemulsification procedures typically include the use of a handpiece for inserting a sleeved needle through a corneal incision and thereafter vibrating the needle in order to emulsify hard nuclear material of the cataract lens. The incision is generally made in the region of the limbus or in the cornea.

An annulus formed between the sleeve and the needle functions as a passage which allows for the introduction, or inflow, of the saline fluid into the eye for irrigation.

The saline fluid prevents the cornea from collapsing as the lens material is emulsified and aspirated. In addition, the saline irrigation fluid aids in the aspiration of emulsified cataract lens material from the eye. The aspiration is conducted through the hollow center of the vibrating needle. The handpiece and needle are connected with an external power source, an irrigation fluid source, and a vacuum source. A control system provides for coordinated ultrasonic vibration, irrigation and aspiration of fluids to and from the eye.

Heretofore, irrigation fluid pressure has been established through the use of an elevated bottle, which provides a source of saline solution. It should be appreciated that fluid control and eye pressure are of utmost importance. Corresponding irrigation and aspiration of flow rates as hereinabove noted are used to maintain the eye in an inflated, pressurized condition during cataract removal. However, the incision size is important since it provides an alternate route for leakage of fluid from the eye.

This leakage causes diminished inflation of the eye during cataract surgery and occurs between the edges of the incision and exterior surfaces of sleeved needle. During the phacoemulsification procedure, the needle is manipulated and such manipulation can lead to wound stretching. This, in turn, changes the leakage rate from the eye and compounds the problem of balanced irrigation and aspiration fluid flow and the maintenance of a proper pressure state of the eye during surgery.

Accordingly, variation in wound construction, sleeve/incision geometry and needle size are important as they relate to fluid leakage from the wound. Deflation of the eye, which may be caused by such leakage, may cause certain tissue within the eye to collapse within one another or on the sleeved needle extending into the eye. In this manner, fluid loss may cause damage to the cornea, iris, or lens capsule which surround the cataract.

One method for counteracting fluid leakages as to increase the amount of irrigation and aspiration fluid flow which is inconveniently done through raising and lowering of the irrigation source bottle along with a concomitant adjustment in aspiration rate.

Accordingly, there is a need for a system for coordinating irrigation fluid flow and aspiration flow during ophthalmology surgery procedures. The present invention fills that need.

SUMMARY OF THE INVENTION

A method for controlling fluid flow to and from an eye during ophthalmic surgery includes introducing irrigation fluid into an eye and aspirating fluid from the eye. During fluid flow initial irrigation fluid pressure is determined. Irrigation fluid flow, aspiration fluid flow and maximum vacuum is adjusted based on the determined initial irrigation fluid pressure. Thereafter irrigation fluid pressure is continuously determined and irrigation fluid flow, aspiration fluid flow and maximum vacuum is continuously adjusted based on the continuous determination of irrigation fluid pressure.

A handpiece suitable for use in phacoemulsification procedures while producing the method of the present invention, generally includes an ultrasonically driven, hollow, sleeved needle and the method, in accordance with the present invention, further includes the steps of inserting the needle and sleeve into an eye for phacoemulsification of eye tissue. Irrigation fluid is introduced into the eye through an annulus established between the sleeve and the needle and fluid is aspirated from the eye through the hollow needle.

An initial irrigation fluid pressure is determined and in response thereto irrigation fluid flow and aspiration fluid flow are adjusted in order to initially maintain proper eye pressure within the eye.

Thereafter, irrigation pressure is continuously determined and in response thereto, the irrigation flow and aspiration fluid flow are adjusted based upon the continuous determination of irrigation fluid pressure. Importantly, the method does not include the raising and lowering of a bottle of irrigation fluid as is necessary in prior art methods. The present invention is also distinguished from prior art method in that the fluid flow rates are automatically regulated, or adjusted based upon irrigation fluid pressure determination. This is to be distinguished from current method in which control of irrigation fluid is maintained by feedback from a surgeon based upon visual observation of tissue under the affects of irrigation. In addition, the surgeon control of irrigation is limited to an on/off control valve and adjustment of the irrigation fluid source height.

In the present invention, the introduction of irrigation fluid into an eye is performed through the use of a positive displacement pump and the step of adjusting the irrigation fluid flow includes adjusting the pump speed.

The determination of irrigation fluid pressure many be done through the use of a transducer disposed in a line interconnecting the pump and handpiece or through direct measurement of pressure within the eye.

The adjustment of aspiration fluid flow may include setting a maximum aspiration vacuum pressure as a function of determined irrigation fluid pressure. More particularly, this maximizes aspiration vacuum may be a linear function of the determined irrigation fluid pressure.

The change of irrigation fluid pressure may also be utilized in accordance with the present invention for providing an indication of wound leaking.

The apparatus in accordance with the present invention for controlling fluid flow to and from a phacoemulsification handpiece in order to accommodate changes in incision size and would stretching during eye surgery generally includes a supply of irrigation fluid and a positive displacement pump for introducing irrigation fluid from the supply of irrigation fluid into an eye through an annulus established between a sleeve and a needle of a handpiece.

A vacuum source is provided for aspirating fluid from the eye through the hollow portion of the needle and a pressure sensor is provided for determining pressure of irrigation fluid introduced into the eye.

A control system is provided for adjusting irrigation fluid and the aspiration fluid flow rates in response to the determined irrigation flow pressure. More particularly, the pressure sensor may be disposed in a line interconnecting the positive displacement pump in the needle or a pressure sensor disposed in the eye.

The control system may also include an indication for enabling monitoring by a surgeon of wound construction consistency based upon irrigation of fluid pressure.

BRIEF DESCRIPTION OF THE DRAWINGS

The present invention may be more clearly understood with reference to the following detailed description, in connection with the appended drawings, in which.

DETAILED DESCRIPTION

Figure 1:
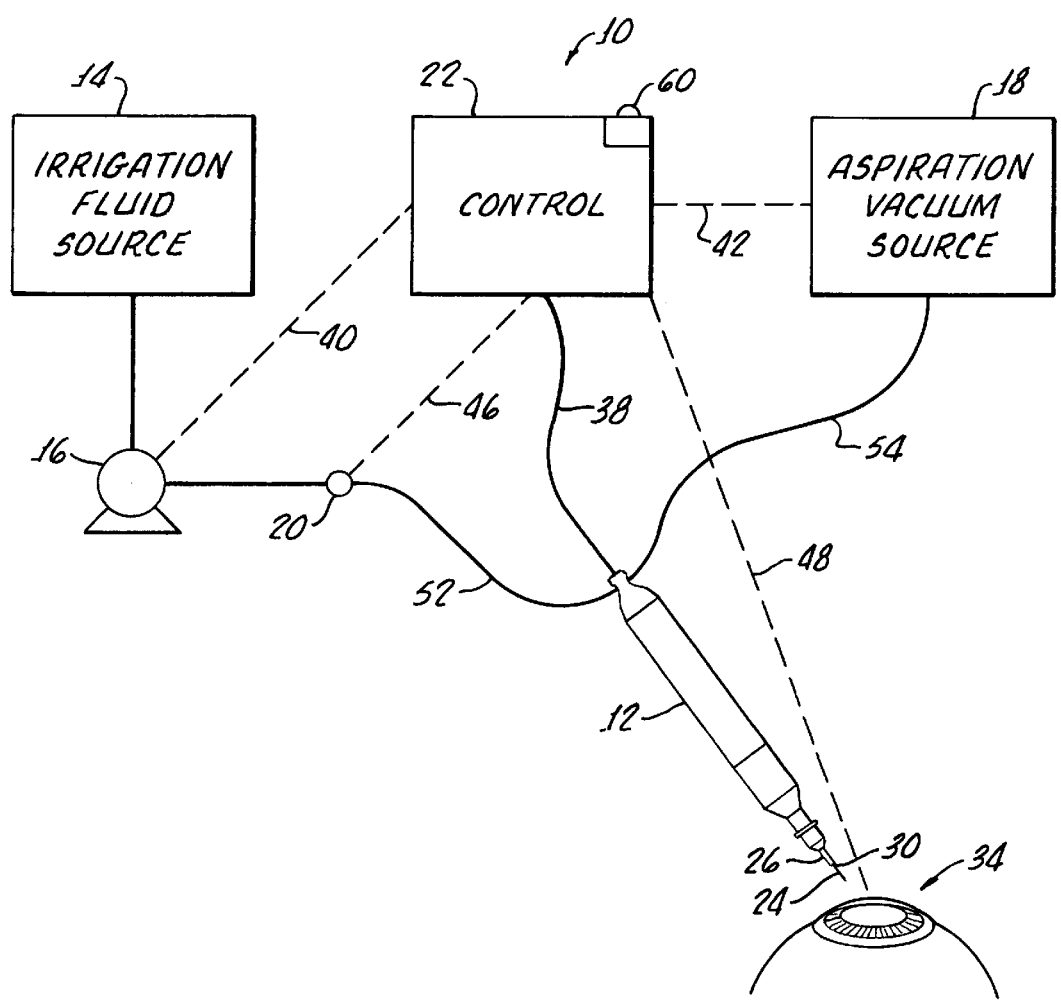
FIG. 1 is a diagram illustrating apparatus and method in accordance with the present invention.

With reference to FIG. 1, there is shown apparatus 10 in accordance with the present invention for controlling fluid flow to and from a phacoemulsification handpiece 12 which generally includes a supply 14 of irrigation fluid, a positive displacement pump 16, a vacuum source 18, a pressure sensor 20 and a control system 22 described hereinafter in greater detail and also suitable for performing the method of the present invention.

It should be appreciated that while a phacoemulsification handpiece 12 is described herein for the practice of the present invention, for illustration purposes, other surgical instruments (not shown) may be utilized for different ophthalmic surgical procedures and separate infusion and aspiration needles (not shown) may be used for practice of the present invention.

The handpiece 12, which may be of any conventional type, includes an ultrasonically driven, hollow needle 24 having a sleeve 26 thereabout which establishes an annulus 30 round needle for introducing irrigation fluid into an eye 34 in a conventional manner.

By utilizing the pump 16 which preferably is a positive displacement pump in combination with the pressure sensor 20, a "closed" pressure measurement system is provided which enables the precise control of infusion pressure into the eye without relying on the height of a traditional irrigation fluid source (not shown). Preferably a bi-directional positive displacement pump 16 facilitates precise control of the fluid pressure.

The control system 22 provides electrical power to the handpiece 12 for ultrasonically driving the needle 24 through line 38. Through lines 40, 42 the control system 22 controls the pump 16 speed and a vacuum source 18 respectively. The aspiration vacuum source 18 may be of any conventional type and include as, for example, a peristaltic pump. Input to the control system 22 from the sensor 20 is provided through a line 46 or a line 48 from a sensor (not shown) disposed within the eye.

The sensor 20 is disposed in an irrigation line 52 between the pump 16 and the handpiece 12. Aspiration from the handpiece 12 and hollow needle 24 to the vacuum source 18 occurs through the line 54.

The pressure transducer 20 may be a medical grade compensated sensor pressure which is available from Motorola. Alternatively direct irrigation fluid pressure measurement may be made by a transducer directly from the eye. A suitable transducer for this mode of operation, is also which is available from Motorola. The control system 22 includes software for conducting the function and method of the apparatus as hereinafter described.

A method for controlling fluid flow to and from a phacoemulsification handpiece 12 in order accommodate changes in incision size and wound stretching, for example, during eye surgery, generally includes a step of inserting the needle 24 into the eye for phacoemulsification of eye tissue. Irrigation fluid is introduced into the eye through the annulus 30 established between the sleeve 26 and the needle 24. Aspiration of the fluid from the eye 34 is then conducted through the hollow needle handpiece 12 and line 54 to the aspiration vacuum source 18.

An initial irrigation fluid pressure is determined by the sensor 20 and the irrigation fluid flow from the source 14 is adjusted by the control system 22 through operation of pump 16 based upon a determined initial irrigation fluid pressure as provided by the sensor 20.

Thereafter, the irrigation fluid pressure is continuously determined via the sensor 20 and the irrigation fluid flow and aspiration fluid flow based upon this continuous determination of irrigation fluid pressure is provided by the control system through the lines 40,42 respectively to the pump 16 aspiration vacuum source 18.

A variation in wound construction, sleeve/incision geometry and needle size are then mediated by monitoring the pressure present at either the surgical site or the sensor 20. A leaking wound can be compensated for by adjustment of fluid flow by the control system 22.

Figure 2:
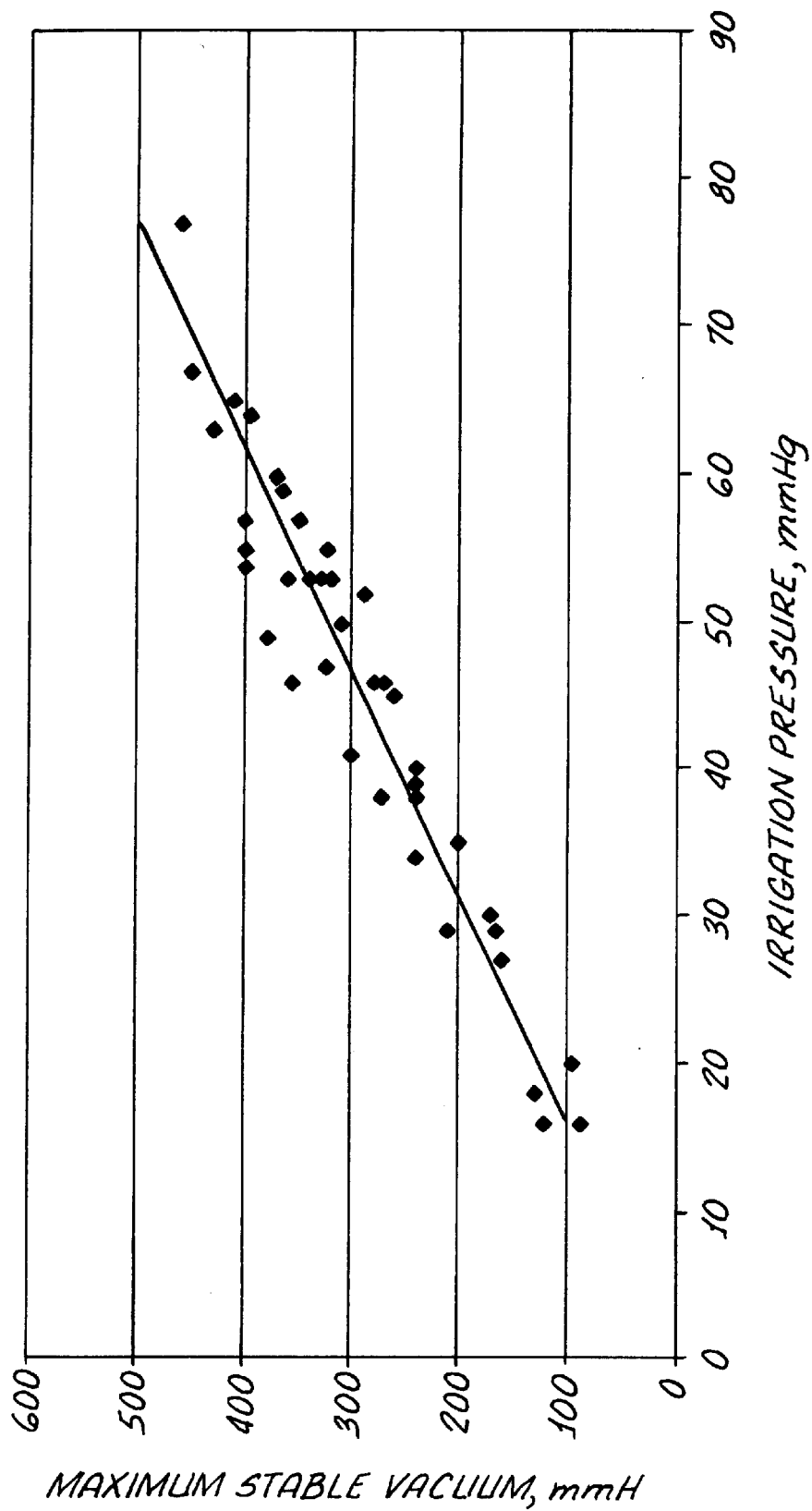
FIG. 2 is a plot of maximum stable vacuum corresponding to measured irrigation pressure which may be utilized by the control system shown in FIG. 1 for making fluid flow changes.

It has been found that maximum usable vacuum is a function of irrigation fluid pressure. This relationship is shown in FIG. 2. In FIG. 2, the data shows a clear trend of increased usable vacuum with an increased irrigation pressure. This data is derived from various combinations of sleeves, needles and incision sizes in a laboratory model (not shown).

This relationship can be incorporated as an algorithm in the control system 22 software. Accordingly, the control system 22 can provide a maximum vacuum setting shown on the Y axis on the plot shown in FIG. 2 as a basis of a measured irrigation pressure. In addition, the control system 22 may include an indicator 60 which may be visible or audible for enabling a surgeon to monitor wound construction consistency based upon monitoring of irrigation fluid pressure, and changes thereto during phacoemulsification procedures.

Although there has been hereinabove described a method and apparatus for controlling fluid flow to and from an eye or phacoemulsification handpiece in accordance with the present invention, for the purpose of illustrating the manner in which the invention may be used to advantage, it should be appreciated that the invention is not limited thereto. Accordingly, any and all modifications, variations and equivalent arrangement which may occur to those skilled in the art should be considered to be within the scope of the present invention as defined in the appended claims.

What is claimed is:

1. Apparatus for controlling fluid flow to and from an eye, said apparatus comprising:

a supply of irrigation fluid;

a positive displacement pump for introducing irrigation fluid from said supply of irrigation fluid into an eye;

a vacuum source for aspirating fluid from the eye through a hollow needle;

a pressure sensor for determining pressure of irrigation fluid introduced into the eye; and a control system for adjusting irrigation fluid and aspiration fluid flow rates in response to determined irrigation fluid pressure.

2. The apparatus according to claim 1 wherein said pressure sensor is disposed in a line interconnection, said positive displacement pump and the needle.

3. The apparatus according to claim 1 wherein said control system includes an indicator for enabling monitoring by a surgeon of wound construction consistency based upon irrigation fluid pressure.

* * * * *